US00PP27315P2

(12) United States Plant Patent
Moore

(10) Patent No.: US PP27,315 P2
(45) Date of Patent: Oct. 25, 2016

(54) ***PENSTEMON* PLANT NAMED 'PMOORE14'**

(50) Latin Name: ***Penstemon* hybrid**
Varietal Denomination: Pmoore14

(71) Applicant: Peter R. Moore, Stockbridge (GB)

(72) Inventor: Peter R. Moore, Stockbridge (GB)

( * ) Notice: Subject to any disclaimer, the term of this patent is extended or adjusted under 35 U.S.C. 154(b) by 0 days.

(21) Appl. No.: 14/545,880

(22) Filed: Jun. 30, 2015

(51) Int. Cl.
*A01H 5/02* (2006.01)

(52) U.S. Cl.
USPC ..... Plt./465

(58) Field of Classification Search
USPC ..... Plt./465
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of interspecific *Penstemon* plant named, 'Pmoore14', that is characterized by its upright, sturdy, uniform plant habit, its sturdy leaves that are medium to dark green in color, its strong flower spikes with evenly spaced flowers, and its large flowers that are deep velvety purple in color and lack a tinged throat.

2 Drawing Sheets

Botanical classification: *Penstemon* hybrid.
Cultivar designation: 'Pmoore14'.

BACKGROUND OF THE INVENTION

The present invention relates to a new and distinct cultivar of hybrid *Penstemon* plant, botanically known as *Penstemon* hybrid 'Pmoore14' and will be referred to hereafter by its cultivar name, 'Pmoore14'. The new cultivar represents a new herbaceous perennial grown for garden and landscape use.

The new invention arose from an ongoing controlled breeding program conducted by the Inventor in Longstock, England with the objective of developing new cultivars of *Penstemon* with strong plant habits and large, unique flowers.

'Pmoore14' was derived from a cross made in July of 2007 between an unnamed, proprietary *Penstemon barbatus* plant (not patented) as the female parent and an unnamed, proprietary *Penstemon heterophyllus* plant (not patented) as the male parent. 'Pmoore14' was selected in summer 2009 as a single unique plant from amongst the resulting seedlings.

Asexual propagation of the new cultivar was first accomplished by the Inventor by stem cuttings in October of 2010 in Longstock, England. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Pmoore14' as a unique cultivar of *Penstemon*.

1. 'Pmoore14' exhibits an upright, sturdy, uniform plant habit.
2. 'Pmoore14' exhibits sturdy leaves that are medium to dark green in color.

3. 'Pmoore14' exhibits strong flower spikes with evenly spaced flowers.
4. 'Pmoore14' exhibits large flowers that are deep velvety purple in color and lack a tinged throat.

The female parent is similar to 'Pmoore14' in having flowers that are deep purple in color. The female parent differs from 'Pmoore14' in having a weaker plant habit, flowers that are smaller in size, and in being less floriferous. The male parent is similar to 'Pmoore14' in having strong stems. The male parent differs from 'Pmoore14' in having lighter colored flowers. 'Pmoore14' can be most closely compared to the *Penstemon heterophyllus* cultivar 'Heavenly Blue' (not patented). 'Heavenly Blue' is similar to 'Pmoore14' in having a summer bloom season. 'Heavenly Blue' differs from 'Pmoore14' in having flowers that are pale lilac to blue in color with a tinged throat and in having a larger, more open plant habit.

BRIEF DESCRIPTION OF THE DRAWINGS

The accompanying colored photographs illustrate the overall appearance and distinct characteristics of the new *Penstemon*. The photographs were taken of a plant two years in age as grown outdoors in a 13-cm container in Longstock, England.

The photograph in FIG. 1 provides a side view of a plant of 'Pmoore14' in bloom.

Figure 1:
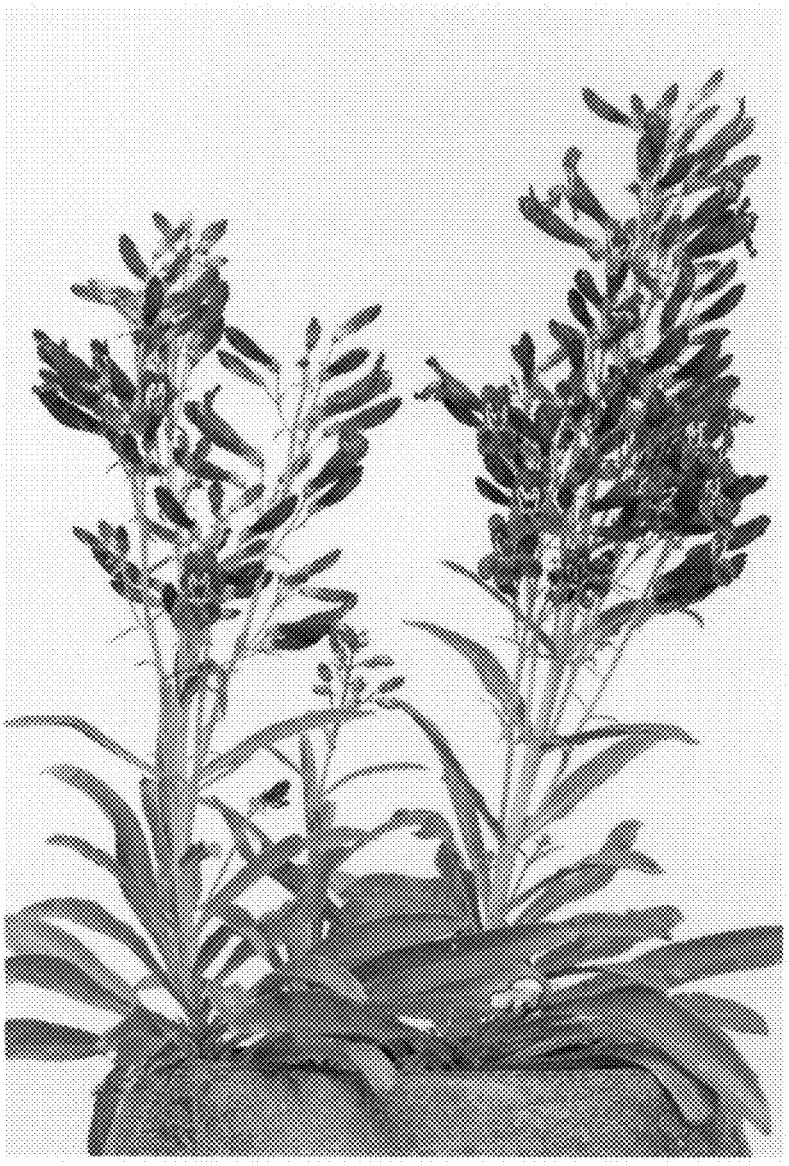
Figure 2:
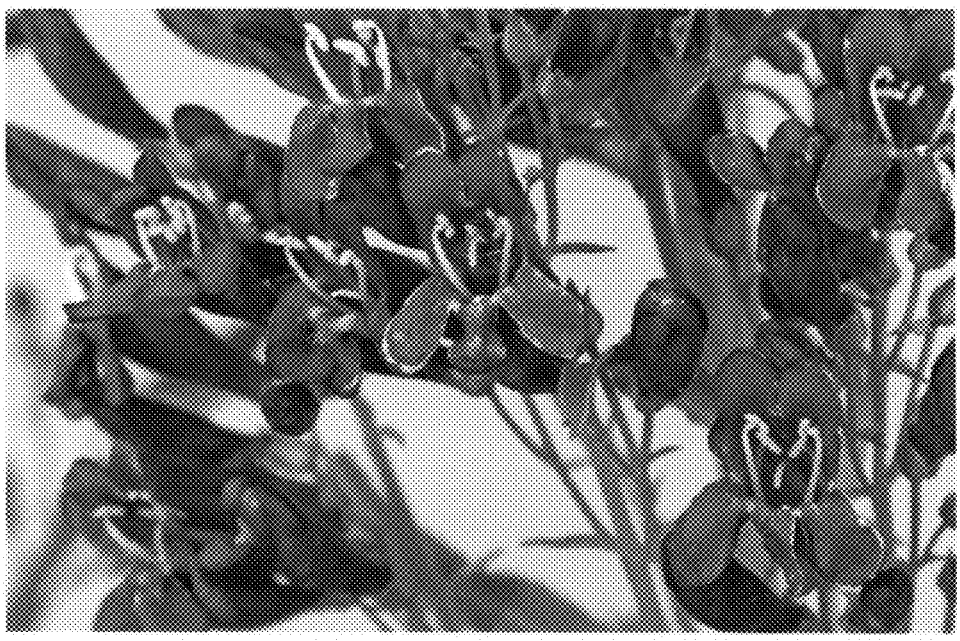

The photograph in FIG. 2 provides a close-up view of the inflorescences of 'Pmoore14'.

Figure 3:
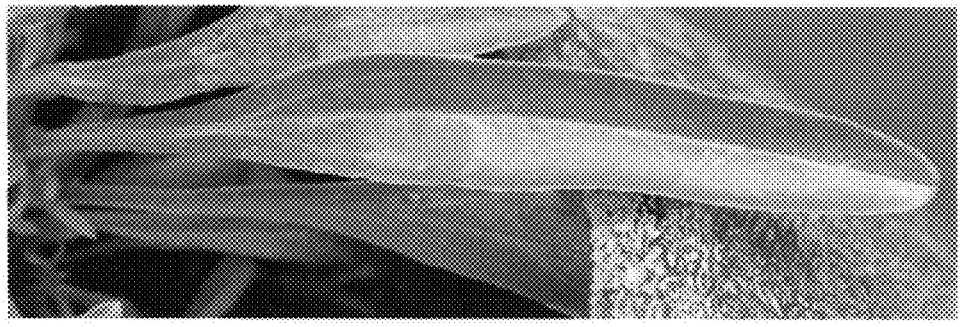

The photograph in FIG. 3 provides a close-up view of the foliage of 'Pmoore14'.

The colors in the photographs are as close as possible with the photographic and printing technology utilized and the color values cited in the detailed botanical description accurately describe the colors of the new *Penstemon*.

DETAILED BOTANICAL DESCRIPTION OF THE PLANT

The following is a detailed description of 2 year-old plants of the new cultivar as grown outdoors in 13 cm containers in Longstock, England. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—June through August in England.

*Plant type*.—Herbaceous perennial.

*Plant habit*.—Upright, sturdy, and uniform.

*Height and spread*.—An average of 36.5 cm in height and 29.5 cm in spread.

*Hardiness*.—U.S.D.A. Zone 8.

*Diseases and pests*.—No disease or pest problems have been observed.

*Root description*.—Deep rooted, fibrous.

Growth and propagation:

*Propagation*.—Stem cuttings.

*Time required for root development*.—An average of two weeks for root initiation about six weeks to produce a young rooted plant.

*Growth rate*.—Moderate.

Stem description:

*Branch habit*.—An average of 3 main flowering stems grow directly from the base of the plant, no lateral branches are present.

*Stem size*.—An average of 17.4 cm (excluding inflorescence) in length and 4 mm in diameter.

*Stem shape*.—Rounded.

*Stem color*.—145C, strongly suffused with 187D at the base.

*Stem surface*.—Smooth, glabrous, and slightly glossy.

*Stem aspect*.—Held at an average angle of 50° to 80° to soil level (=0°=horizontal).

*Stem strength*.—Strong.

*Internode length*.—An average of 1.3 cm, much shorter at the base; an average of 3 mm.

Foliage description:

*Leaf shape*.—Oblanceolate.

*Leaf division*.—Single.

*Leaf size*.—An average of 10.5 cm in length and 1.5 cm in width.

*Leaf quantity*.—About 32 (16 pairs) per stem.

*Leaf shape*.—Oblanceolate.

*Leaf base*.—Long and narrow attenuate.

*Leaf apex*.—Acute.

*Leaf color*.—Young upper surface; 137B and lower surface; 137C, mature upper surface; 137B and lower surface 138B.

*Leaf venation*.—Pinnate pattern, main vein is furrowed, color; upper surface; 144B to 144C, lower surface; 145C.

*Leaf margins*.—Shallowly serrate, teeth pointed towards the base.

*Leaf attachment*.—Sessile.

*Leaf arrangement*.—Opposite, decussate.

*Leaf surface*.—Smooth, glabrous, moderately leathery, and slightly to moderately glossy on both surfaces.

Flower description:

*Inflorescence type*.—Axillary and terminal thyrses.

*Inflorescence size*.—Main stems; an average of 13.8 cm in length and 6.2 cm in width.

*Lastingness of inflorescence*.—About 10 days, self-cleaning.

*Flower size*.—An average of 3 cm in depth and 1.6 to 2 cm in diameter.

*Flower fragrance*.—None.

*Flower number per inflorescence*.—An average of 18 flowers.

*Flower shape*.—Tubular to campanulate with two free upper lobes and three free lower lobes.

*Flower aspect*.—Outward to slightly upright.

*Flower buds*.—Narrow obovate in shape, an average of 2.3 cm in length and 0.4 cm in width, color; upper surface 79A, lower surface 79C, tip suffused with N78A.

*Flower petals*.—An average of 5, narrow spathulate in shape, entire margins, obtuse apex, fused based (lower 66%), an average of 3 cm in length and 4 mm in width, upper lobes curved to a 50° angle to the tube, lower lobes curved to a 115° angle to the tube, upper surface (inside); moderately velvety, smooth, and with a few soft hairs at the base of the lower lobes; an average 1 mm in length and NN155D in color, lower surface texture (outside); dull, slightly velvety and smooth, color: upper surface when opening; upper lobes; a blend between N88A and 90A, lower lobes; 83A suffused with N78A, lower surface when opening; upper lobes N88A, lower lobes; a blend between 77A and N79A, upper surface when fully opened; upper lobes; a blend between N88A and 90A, lower lobes; 83A suffused with N78A, lower surface when fully opened; upper lobes; N88A, lower lobes a blend between 77A and N79A, color fades to 72A on upper lobes and 79C on lower lobes.

*Sepals*.—An average of 5, rotate, ovate in shape, entire margin, acute apex, base fused into a campanulate shape, an average of 6 mm in length and 2.5 mm in width, 144B in color, glabrous and glossy surface texture with hairs on margins.

*Calyx*.—Rotate, an average of 6 mm in length and 4 mm in diameter, 144B in color.

*Peduncle*.—Rounded in shape, an average of 11.6 cm in length and 3 mm in width, strong in strength, 145C in color, axillary peduncles held at an average of 15° to main stem, terminal peduncles held at an average angle of 0° to main stem branch, satiny, glabrous, and smooth surface texture.

*Pedicel*.—Rounded in shape, an average of 1 cm in length and 1 mm in diameter, moderately strong in strength, 144C in color, held at an average angle of 20° to peduncle, satiny, glabrous and smooth surface texture.

Reproductive organs:

*Gynoecium*.—1 Pistil, an average of 2.1 cm in length; style; an average of 2 cm in length is 77B with. base NN155C to NN155D in color; stigma; narrow, club-shaped and pointed upwards, N155A in color, ovary; 144C in color.

*Androcoecium*.—4 stamens, diadelphous (2 short stamens and 2 longer stamens), filament; an average of 2 cm or 2.2 cm in length and N155B in color; anther; an average of 2 mm in length, dorsifixed, elliptic in shape, and 161C in color, pollen is low in quantity and 158C to 158D in color.

*Fruit and seed*.—No fruit or seed production has been observed.

It is claimed:

1. A new and distinct cultivar of *Penstemon* plant named 'Pmoore14' as herein illustrated and described.

* * * * *